(12) United States Patent
Starkebaum et al.

(10) Patent No.: US 7,282,050 B2
(45) Date of Patent: Oct. 16, 2007

(54) ABLATION OF EXTERIOR OF STOMACH TO TREAT OBESITY

(75) Inventors: Warren L. Starkebaum, Plymouth, MN (US); Thomas R. Prentice, Lake Elmo, MN (US); Mark A. Christopherson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 168 days.

(21) Appl. No.: 10/699,207

(22) Filed: Oct. 31, 2003

(65) Prior Publication Data

US 2005/0096638 A1    May 5, 2005

(51) Int. Cl.
*A61B 18/18* (2006.01)
(52) U.S. Cl. .......................... 606/41; 128/898; 607/101
(58) Field of Classification Search ................ 606/41, 606/49, 50, 32, 40; 607/96, 98, 100, 101, 607/104, 105; 128/898
See application file for complete search history.

(56) References Cited

U.S. PATENT DOCUMENTS

| | | | |
|---|---|---|---|
| 4,279,906 A | 7/1981 | Frosch et al. | |
| 4,869,902 A | 9/1989 | Buehler et al. | |
| 5,188,104 A | 2/1993 | Wernicke et al. | |
| 5,403,326 A | 4/1995 | Harrison et al. | |
| 5,423,872 A | 6/1995 | Cigaina | |
| 5,505,730 A | 4/1996 | Edwards | |
| 5,569,241 A | 10/1996 | Edwards | |
| 5,782,798 A | 7/1998 | Rise | |
| 5,827,273 A | 10/1998 | Edwards | |
| 6,159,146 A | 12/2000 | El Gazayerli | |
| 6,183,776 B1 | 2/2001 | Depui et al. | |
| 6,405,732 B1 | 6/2002 | Edwards et al. | |
| 6,425,877 B1 | 7/2002 | McGuckin et al. | |
| 6,427,082 B1 | 7/2002 | Nordstrom et al. | |
| 6,427,089 B1 | 7/2002 | Knowlton | |
| 6,802,840 B2 * | 10/2004 | Chin et al. | 606/41 |
| 6,826,428 B1 * | 11/2004 | Chen et al. | 607/40 |
| 2002/0183768 A1 | 12/2002 | Deem et al. | |
| 2003/0040804 A1 | 2/2003 | Stack et al. | |
| 2003/0153905 A1 * | 8/2003 | Edwards et al. | 606/41 |

FOREIGN PATENT DOCUMENTS

WO    WO 00/69376    11/2000
WO    WO 01/87335    11/2001

OTHER PUBLICATIONS

"Stomach 'Pacemaker' May Suppress Appetite," story.news.yahoo.com/news?tmpl=story&cid=541&e=6&u=/ap/tummy_pacemaker, 2003.

* cited by examiner

*Primary Examiner*—Michael Peffley
(74) *Attorney, Agent, or Firm*—Mary P. Bauman

(57) ABSTRACT

The invention provides methods and devices to treat obesity by ablating tissue from an exterior surface of a stomach of a patient. For example, the invention may involve ablation of exterior stomach tissue to alter gastric myoelectric activity or muscle function from the exterior surface of the stomach to produce abnormal gastric peristalsis without damaging the mucosal lining of the stomach. The invention may further provide methods and devices to monitor the gastric myoelectric activity before and after the ablation procedure.

7 Claims, 5 Drawing Sheets

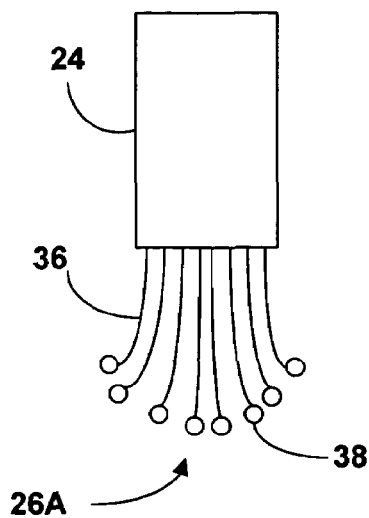
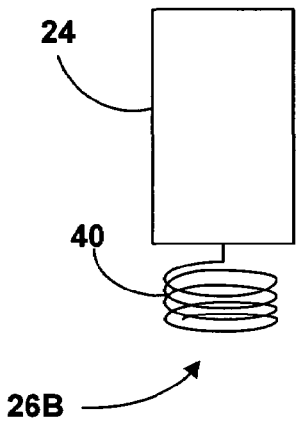
FIG. 2
FIG. 3
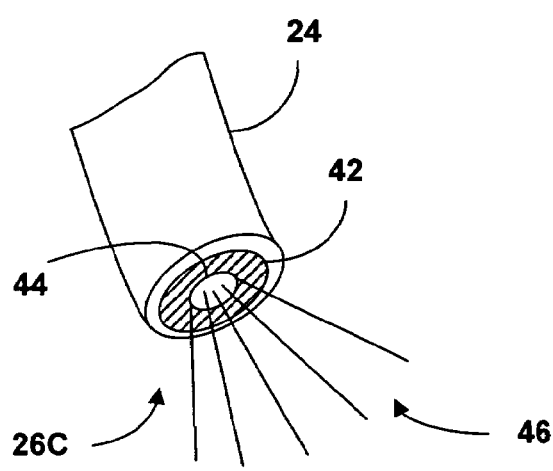
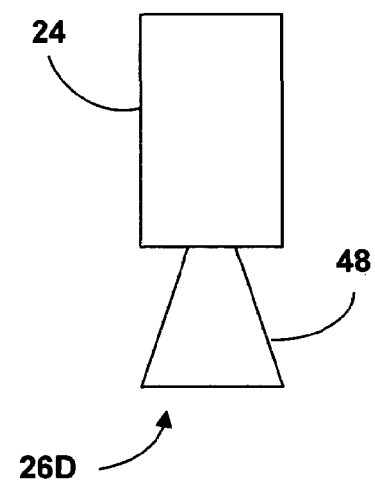
FIG. 4
FIG. 5

ABLATION OF EXTERIOR OF STOMACH TO TREAT OBESITY

FIELD OF THE INVENTION

The invention relates generally to surgical techniques affecting the stomach, and, more particularly, to surgical techniques for treatment of obesity.

BACKGROUND

A variety of medical approaches have been devised for treatment of obesity, including diet, medication and surgery. In general, surgery is reserved for patients in whom conservative measures, such as monitoring caloric intake or controlling appetite with appetite suppressants, have failed. In addition, surgery is generally reserved for patients who are seriously overweight.

There have been many surgical approaches to obesity. For example, some patients have received implantation of one or more bulking prostheses to reduce stomach volume. The prosthesis limits the amount of food the stomach can hold and causes the patient to feel full. U.S. Published Patent Application No. 20030040804 to Stack et al., for example, describes a tubular prosthesis that induces feelings of satiety within a patient. Another approach is restrictive surgery, which surgically makes the stomach smaller by removing or closing a section of the stomach. This procedure also causes the patient to feel full. U.S. Published Patent Application No. 20020183768 to Deem et al., which describes a recent proposal for treating obesity, describes various techniques for reducing the size of the stomach pouch to limit caloric intake as well as to provide an earlier feeling of satiety.

Another surgical procedure to treat obesity is the gastric bypass procedure. In the gastric bypass procedure, the surgeon creates a small stomach pouch to restrict food intake and constructs a bypass of the duodenum and other segments of the small intestine. This procedure limits the amount of food that is completely digested or absorbed. Surgical interventions such as these are very invasive, and each form of surgery may involve complications. Restrictive surgery may entail a risk of vomiting, for example, and gastric bypass surgery may result in unpleasant consequences known as "dumping syndrome."

Another technique for treatment of obesity involves administration of therapeutic agents, such as drugs. For example, extensive research and development has been conducted with respect to appetite suppressants, resulting in limited efficacy and, in many cases, undesirable side effects. Also, PCT Publication No. WO/0187335 to Uhlman et al. describes administration of agents to selectively inhibit ghrelin activity. Recent studies suggest that ghrelin is a potent appetite stimulant in animals and man when administered orally.

Another surgical technique is described in U.S. Pat. No. 6,427,089 to Knowlton. In particular, Knowlton describes a surgical technique for causing a contraction or reduction in the volume of the stomach by the delivery of thermal energy to the stomach wall. According to Knowlton, the technique relies on a microwave device to heat a submucosal layer of tissue within the stomach wall without thermal damage of the mucosa of the stomach. A resulting thermal lesion causes contraction of the preexisting collagen matrix of the stomach wall. A further technique is described in PCT Publication No. WO 00/69376 to Edwards in which nerves responsible for the sensations of hunger are ablated by applying energy to the interior mucosal lining of the stomach. The mucosal lining of the stomach, which is responsible for protecting the stomach tissue and producing stomach acid necessary for digestion, is ablated along with the specified nerves.

Table 1 below lists documents that disclose techniques for treatment of obesity.

TABLE 1

| Patent Number | Inventors | Title |
| --- | --- | --- |
| 20020183768 | Deem et al. | Obesity treatment tools and methods |
| 20030040804 | Stack et al. | Satiation devices and methods |
| WO/0187335 | Uhlman et al. | Method for selectively inhibiting ghrelin action |
| 6,427,089 | Knowlton | Stomach treatment apparatus and method |
| 5,782,798 | Rise | Techniques for treating eating disorders by brain stimulation and drug infusion |
| WO 00/69376 | Edwards | Surgical weight control device |
| 5,423,872 | Cigaina | Process and device for treating obesity and syndromes related to motor disorders of the stomach of a patient |
| 5,188,104 | Wernicke et al. | Treatment of eating disorders by nerve stimulation |

All documents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY

The present invention is directed to devices and methods for treating obesity. The invention has certain objects. That is, various embodiments of the present invention provide solutions to one or more problems existing in the prior art with respect to treatment of obesity.

The problems include, for example, the limited efficacy and side effects of conventional appetite suppressant medications, and the need for potential repeated dosages of such medications by the patient. Additional problems relate to the general undesirability, invasiveness, infection risk, and recovery time associated with conventional surgical techniques for treatment of obesity, such as gastric reduction and bypass surgery, and other techniques for altering the shape or size of the stomach. Side effects of some invasive procedures, such as vomiting and "dumping syndrome," are also undesirable. Further problems relate to the need for chronic implant of prostheses within the stomach to induce satiety. Other problems relate to damage suffered by the mucosal layer of the stomach after internal stomach ablation for appetite suppression.

Various embodiments of the present invention have the object of solving at least one of the foregoing problems. For example, objects of the present invention provide methods and devices for treating obesity that involve altering gastric myoelectric activity or muscle function from the exterior surface of the stomach to produce abnormal gastric peristalsis without damaging the mucosal lining of the stomach. As examples, objects of the invention include the ability to alter myoelectric activity within regions of the stomach responsible for regulation of myoelectric activity, alter vagal nerve function within the stomach, and directly alter gastric muscle function from the exterior stomach surface. These objects may be attained by laparoscopic surgery, which uses several small incisions instead of one large incision.

Various embodiments of the invention may possess one or more features capable of fulfilling the above objects. In general, the invention provides a method for treating obesity that involves ablating tissue from an exterior surface of a stomach of a patient with an ablation probe sized for use with the stomach. The ablation of stomach tissue is carried out in order to alter the gastric myoelectric activity. The gastric myoelectric activity may be monitored before and after ablation to determine the success of the ablation.

In particular, the method may involve ablation of cells in various regions of the stomach to produce abnormal gastric peristalsis that may be effective in suppressing appetite. The frequency of gastric peristaltic activity is controlled by the so called gastric slow wave, which originates in the pacemaker region of the corpus of the stomach and propagates slowly toward the antrum, repeating roughly three times per minute. By altering the gastric myoelectric function of the stomach, gastroparesis can be induced to cause slow gastric emptying and cause a feeling of satiety to persist in obese patients.

Additional embodiments are directed to the ablation of stomach tissue in the submucosal plexus, myenteric plexus, or both, to destroy cells that regulate myoelectric activity to cause abnormal gastric peristalsis and thereby induce symptoms of gastroparesis. As another alternative, the invention provides ablation of gastric muscle to inhibit muscle activity and cause abnormal gastric peristalsis. Abnormal peristalsis by ablation of gastric muscle results in symptoms of gastroparesis, and thereby causes the patient to lose weight. As a further alternative, the invention provides features relating to ablation of stomach tissue to disrupt the function of the vagal nerve, inducing symptoms of gastroparesis and causing weight loss.

Devices for ablation of stomach tissue for alteration of gastric myoelectric activity may include a wide range of gastric ablation probes. The gastric ablation probe is inserted into an abdomen of a patient via a cannula used in laparoscopic surgery. In general, the gastric ablation probe is sized for use with the stomach to provide contact or non-contact ablation of selected regions of the exterior stomach lining.

The ablation probe may take the form of an electrode or array of electrodes for transmission of radio frequency electrical current, optical waveguide for delivery of laser energy, a microwave antenna, a cryogenic probe, an internally heated probe, or the like. In addition, in some embodiments, the ablation probe may include a fluid delivery port for delivery of fluids to the ablation site for enhanced conductivity or cooling. The ablation level and depth can be controlled to selectively ablated different tissue regions of the stomach and thereby achieve desired effects in treating obesity.

In comparison to known implementations for treatment of obesity, various embodiments of the present invention may provide one or more advantages. For example, the invention avoids the need for highly invasive, surgical alteration or reconstruction of the stomach, as presented by gastric reduction and bypass procedures, as well as associated patient recovery times. In addition, the invention does not require the implantation of a prosthesis, or administration of medication with uncertain efficacy and prolonged dosage requirements. Further, the invention does not require the ablation of the protective interior lining of the stomach. Rather, the invention provides a laparoscopic surgical ablation treatment that alters myoelectric activity from the exterior surface of the stomach to suppress appetite and thereby treat obesity.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 2 illustrates an ablation probe comprising a plurality of flexible, electrically conductive filaments.

FIG. 3 illustrates an ablation probe comprising a flexible, helical or spiral wound conductive coil.

FIG. 4 illustrates an ablation probe comprising an electrode and a fluid delivery port.

FIG. 5 illustrates an ablation probe comprising a waveguide.

DETAILED DESCRIPTION OF THE PREFERRED EMBODIMENTS

Figure 1:
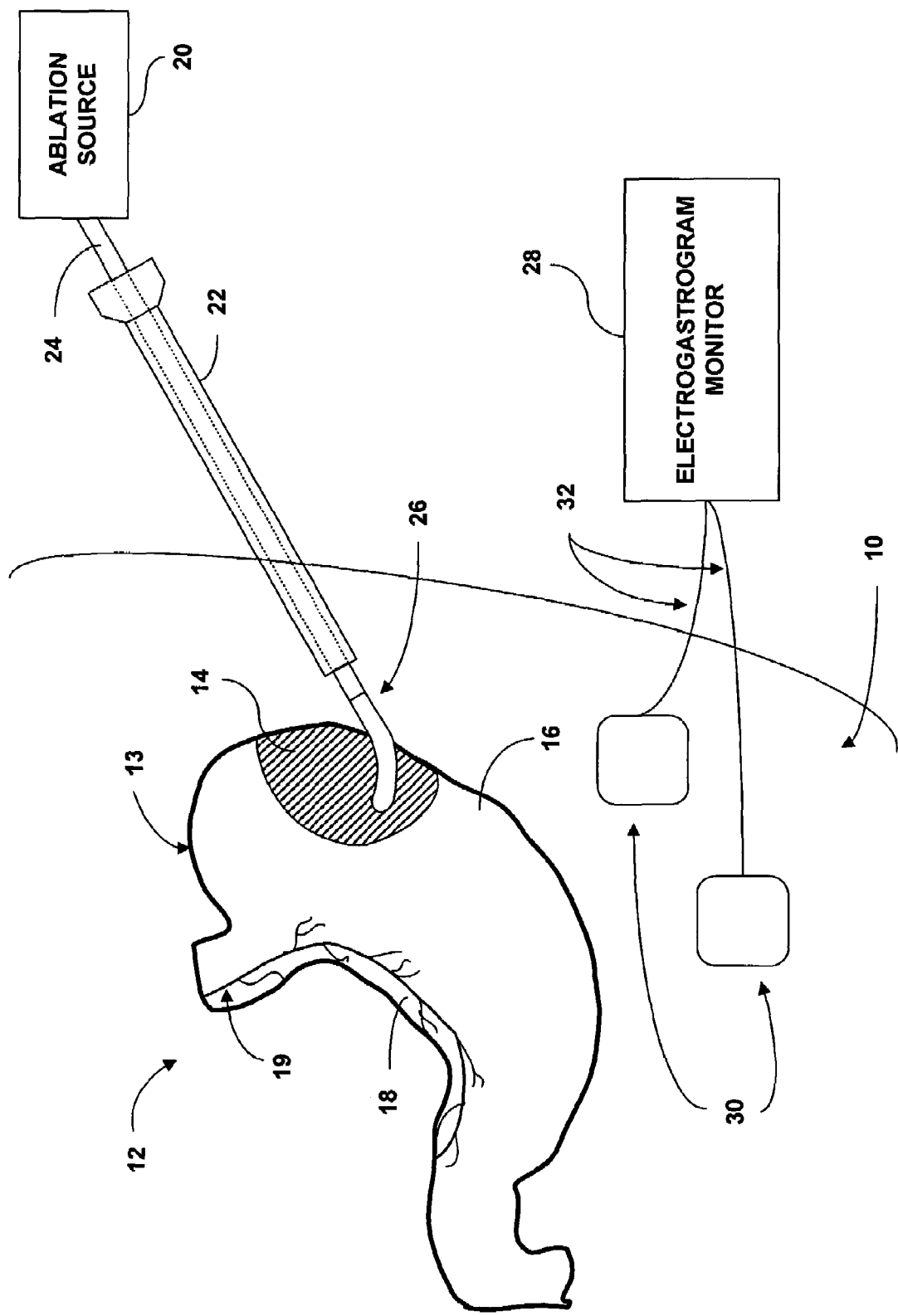
FIG. 1 is a schematic diagram illustrating a tissue ablation system for ablating an exterior surface of a stomach to treat obesity.

FIG. 1 is a schematic diagram illustrating a tissue ablation system for ablating an exterior surface 13 of a stomach 12 to treat obesity. As shown in FIG. 1, the ablation system uses a laparoscopic surgery technique to reach exterior surface 13 of stomach 12. In laparoscopic surgery, the patient receives general anesthesia and one or more small incisions are made in an abdomen 10 of the patient. Abdomen 10 is inflated with carbon dioxide so a surgeon can see the abdominal organs. There are multiple targets for ablation of stomach 12 shown in FIG. 1, including, for example, a pacemaker region 14, a greater curvature 16, a lesser curvature 18, and a vagus nerve 19. Ablating tissue at one or more targets 14, 16, 18, and 19 may alter myoelectric activity in stomach 12. Altering the myoelectric activity may slow a peristaltic wave of stomach 12, which reduces digestion rate and therefore causes a feeling of satiety to persist. In this way, altering the myoelectric activity of stomach 12 suppresses the appetite of the patient, causing the patient to consume less and lose weight.

As shown in FIG. 1, the ablation system includes an ablation source 20 to control delivery of ablation energy to an ablation probe 26 via a conductor 24. Ablation source 20 may comprise at least one of a radio frequency, laser, ultrasonic, microwave, thermal, chemical, mechanical, and cryogenic source for use with an appropriate ablation probe. Ablation probe 26 and conductor 24 are inserted into an abdomen 10 of a patient through a cannula 22 during laparoscopic surgery. Ablation probe 26 is sized to fit stomach 12 of the patient, accordingly cannula 22 is sized to fit ablation probe 26. Ablation probe 26 may be flexible or curved to further conform to a shape of the stomach at the target region. As will be described, ablation probe 26 may comprise any of a variety of ablation probes that conform to ablation source 20, for example an electrode for transmission of radio frequency electrical current, an optical waveguide for delivery of energy from a laser, a microwave antenna, a cryogenic probe, an internally heated probe, or the like. In addition, in some embodiments, ablation probe 26 may include a fluid delivery port for delivery of fluids to the ablation site for enhanced conductivity or cooling. In other embodiments, ablation probe 26 includes at least one vacuum port to immobilize a portion of exterior surface 13 prior to ablation.

The ablation system shown in FIG. 1 further includes an electrogastrogram (EGG) monitor 28 with electrodes 30 applied to abdomen 10 over stomach 12 of the patient and coupled to EGG monitor 28 via conductors 32. In other embodiments, electrodes 30 may be embedded into muscle layers of stomach 12, or placed on exterior surface 13 of the stomach. EGG monitor 28 records the electrical signals that travel through the muscle layers of stomach 12 and control contraction and therefore digestion rate. Prior to ablating stomach 12, a baseline digestion rate is determined for the patient by, for example, monitoring the myoelectric activity with EGG monitor 28. The invention encompasses other techniques for determining the baseline digestion rate as well, and is not limited to EGG monitor 28. Furthermore, the baseline digestion rate may be determined by monitoring a specific digestion process, such as gastric emptying. Accordingly, a baseline digestion rate may be reflected in a baseline rate of gastric emptying.

A period of time after the ablation, one week for example, a post-ablation digestion rate is determined. The post-ablation digestion rate may be measured in the same fashion as the baseline digestion rate. If EGG monitor 28 was used to measure the baseline digestion rate, EGG monitor 28 may also be used to measure the post-ablation digestion rate. If the baseline digestion rate was reflected in a baseline rate of gastric emptying, the post-ablation digestion rate may be reflected in a post-ablation rate of gastric emptying. The period of time after the ablation allows the gastro-intestinal (GI) tract to fully recover from the effects of the anesthetic used during the laparoscopic surgery. The post-ablation digestion rate is compared to the baseline digestion rate to determine the success of the ablation procedure. The comparison determines whether the digestion rate has been altered by the ablation, and in particular, determines whether the post-ablation digestion rate is slower than the baseline digestion rate. Additional tissue may be ablated if the post-ablation digestion rate is not sufficiently slow. Use of the EGG monitor before and after ablation provides a quantitative check of the effect of ablation to the exterior 13 of stomach 12.

Altering myoelectric activity causes abnormal gastric peristalsis, and symptoms of gastroparesis. The initiation and propagation of slow waves occurs within a network of interstitial cells of Cajal, which have the intrinsic ability to spontaneously depolarize three times each minute. These cells are present in myenteric and submucosal borders of smooth muscle, but have the highest concentration in pacemaker region 14.

Nausea and vomiting are often associated with abnormal gastric rhythms. For example, tachygastria can be induced by illusory self-motion and occurs prior to the onset of nausea. Gastroparesis is a chronic disorder characterized by abnormally slow gastric emptying and is usually associated with gastric dysrhythmias. Patients with gastroparesis experience nausea and/or vomiting with meals. As a consequence, these patients often lose weight or become malnourished and may require supplemental nutrition to obtain daily nutritional requirements. However, ablation of stomach tissue to induce gastroparesis can be effective in achieving weight loss for obese, and especially morbidly obese, patients.

An ablation level and depth can be controlled to selectively ablate different tissue regions within stomach 12 and thereby achieve desired effects in treating obesity. Accordingly, ablation probe 26 may selectively ablate at least one of a submucosal or myenteric plexus, each of which reside at different depths within stomach 12, to destroy cells that regulate myoelectric activity. The submucosal plexus is an area just below a mucosal layer on an upper surface of a gastric muscle, and contains cells that regulate the normal myoelectric activity of the stomach. The myenteric plexus is an area near an outer layer of the gastric muscle that also contains cells that regulate myoelectric activity.

Ablation probe 26 may also be used to ablate gastric muscle, generally located along the greater curvature 16, to inhibit muscle activity and cause abnormal gastric peristalsis. Rather than ablate the tissue that regulates myoelectric activity, ablation probe 26 ablates the muscle itself to alter muscle function and thereby induce gastroparesis. Abnormal peristalsis by ablation of gastric muscle is expected to result in symptoms of gastroparesis, and thereby cause the patient to lose weight.

In another embodiment, ablation probe 26 may be configured and used to ablate submucosal areas containing the vagus nerve 19. Vagus nerve 19 runs down the esophagus and along the lesser curvature 18 of the stomach, and branches multiple times on the exterior surface 13 of stomach 12. By ablating exterior surface 13 along lesser curvature 18 with sufficiently high ablation level settings, ablation probe 26 can disrupt normal vagal nerve functions, and induce symptoms similar to gastroparesis, including reduced appetite. To assess extent of vagal nerve damage, the extent of heart rate variability can be determined from an ECG or Holter monitor (not shown).

In conventional ablation systems, an ablation probe is inserted into a stomach of a patient via an esophagus. In that case, the ablation probe ablates a mucosal lining, or interior surface, of a stomach to reach the interstitial cells of Cajal, gastric muscle, and/or vagus nerve. Ablation of the mucosal lining destroys the protective layer of the stomach and the cells that produce stomach acid necessary for digestion. Applying the ablation probe to the exterior surface of the stomach preserves the mucosal lining, and maintains substantially similar results in treating obesity.

FIGS. 2-9 are schematic diagrams illustrating exemplary ablation probes 26A-26H, respectively, for use with the tissue ablation system of FIG. 1. Cannula 22 and ablation probes 26A-26H may be positioned along exterior surface 13 of stomach 12 using a video camera inserted into abdomen 10 during laparoscopic surgery. Cannula 22 and ablation probes 26A-26H are sized appropriately for use with stomach 12 and may be flexible or curved to further conform to the shape of stomach 12.

FIG. 2 illustrates an ablation probe 26A comprising a plurality of flexible, electrically conductive filaments 36. Each conductive filament 36 is coupled in common to conductor 24 to receive electrical current from ablation source 20, from FIG. 1. Conductive filaments 36 may carry spherical electrodes 38. In operation, when ablation probe 26A is placed in proximity to exterior surface 13 of stomach 12, flexible filaments 36 extend outward and contact numerous points within a region of tissue to deliver electrical current and thereby ablate the tissue over a larger coverage area. The number of filaments 36 may vary. In addition, filaments may be arranged in a brush-like, two-dimensional array to cover a corresponding area of stomach tissue.

FIG. 3 illustrates an ablation probe 26B comprising a flexible, helical or spiral wound conductive coil 40 coupled to conductor 24. Upon contact with exterior surface 13, coil 40 may compress and expand to more readily conform to a region of stomach 12. Coil 40 delivers electrical current from ablation source 20 to exterior surface 13 and ablates the tissue in the stomach region. In other embodiments, coil 40 may have an expanded diameter at its base or its proximal end. In a further embodiment, coil 40 may be a closely wound, conductive coil with a very small diameter. One of the embodiments of coil 40 may be desired over the others to conform to a specific tissue region, or to create ablation sizes or shapes necessary to treat obesity.

FIG. 4 illustrates an ablation probe 26C comprising an electrode 42 and a fluid delivery port 44 coupled to conductor 24. Fluid delivery port 44 is coupled to a fluid source via a lumen within cannula 22, from FIG. 1, and delivers a stream of fluid 46. Electrode 42 delivers electrical current to the exterior stomach tissue 13 via fluid 46. Fluid 46 may be electrically conductive to enhance the ablation result, and may be delivered at ordinary body temperatures or cooled temperatures. In this sense, ablation probe 26C may form a virtual electrode, e.g., as described in commonly assigned U.S. Pat. No. 6,537,272 to Christopherson et al., the entire content of which is incorporated herein by reference.

In some embodiments, ablation probe 26C includes a plurality of electrodes 42 and fluid delivery ports 44. The plurality of electrodes 42 and fluid ports 44 may be arranged in a pattern to enlarge the ablation area or to conform to one of the target regions of stomach 12.

FIG. 5 illustrates an ablation probe 26D comprising a waveguide 48 coupled to conductor 24. In that case ablation source 20 from FIG. 1 comprises a laser, and waveguide 48 further propagates the laser energy to exterior surface 13 of stomach 12. The energy ablates the stomach tissue located within a proximate radius of waveguide 48. Waveguide 48 may comprise a variety of shapes and sizes to propagate specific wavelengths and modes of the laser energy.

Figure 6:
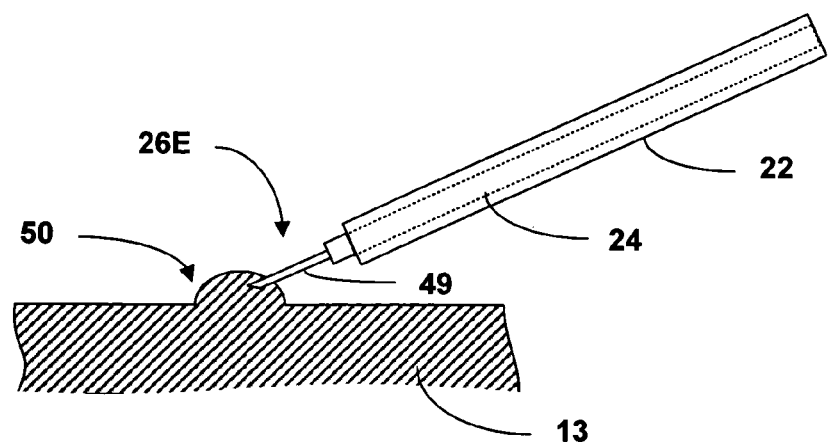
FIG. 6 is a diagram illustrating an ablation probe comprising a radio frequency ablation needle.

FIG. 6 is a diagram illustrating an ablation probe 26E comprising a radio frequency ablation needle 49 carried by conductor 24 via cannula 22. When ablation probe 26E reaches one of ablation targets 14, 16, 18, and 19, from FIG. 1, a surgeon inserts needle 49 into the exterior surface 13. In the example of FIG. 6, needle 49 is a hollow, conductive needle defining an inner lumen for delivery of fluid. In that embodiment, ablation probe 26E forms a virtual electrode within the tissue or manages cooling of surrounding tissue. In particular, electrical current may be accompanied by delivery of precise volumes of electrolytes to yield desired conduction characteristics.

The surgeon delivers the electrolyte fluid, such as saline, into exterior tissue layer 13 via needle 49 to create a "blister" 50. The surgeon then activates ablation source 20, in this case an electrical current generator, to deliver electrical current to blister 50 via needle 49, and thereby ablate the tissue in the vicinity the blister. Alternatively, the surgeon could penetrate deeper into the stomach tissue to form blister 50 within the sub-mucosal layer or the smooth muscle layer.

Figure 7:
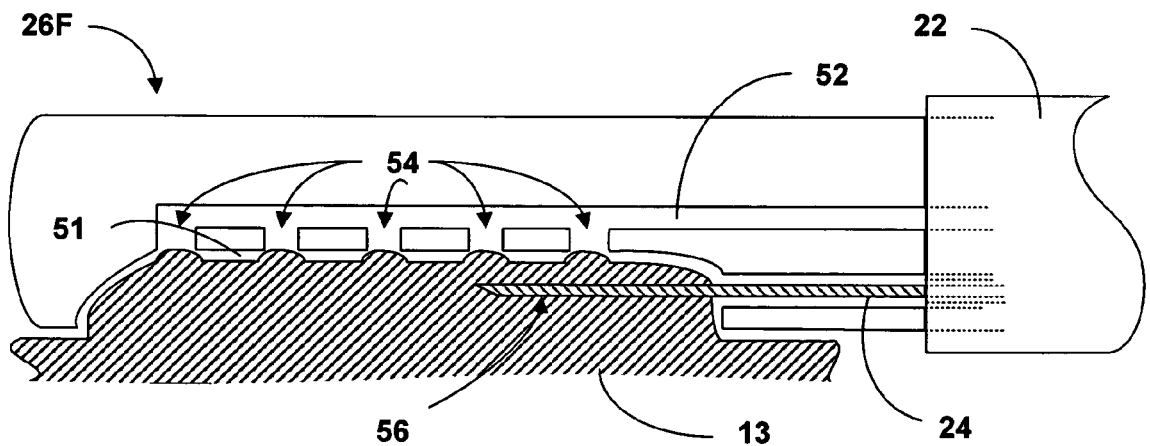
FIG. 7 is a side view illustrating an ablation probe comprising an array of vacuum ports to immobilize a portion of exterior stomach tissue.

FIG. 7 is a side view illustrating an ablation probe 26F comprising an array of vacuum ports 54 to immobilize a portion of exterior stomach tissue 13. Ablation probe 26F includes a cavity 51, a vacuum line 52, vacuum ports 54, and a conductive needle 56. Conductive needle 56 couples to conductor 24 and may be a hollow needle defining an inner lumen for delivery of fluid, as described in reference to FIG. 6. Vacuum line 52 extends through cannula 22 and provides negative pressure from a vacuum source (not shown) to vacuum ports 54.

In general, cavity 51 is sized and shaped to permit capture of a selected amount of stomach tissue by vacuum ports 54 for ablation. For example, cavity 51 may have different depths for selective ablation of exterior tissue 13, submucosal tissue such as submucosal plexus or myenteric plexus, gastric muscle tissue, or tissue containing vagal nerve fibers. In particular, ablation of exterior tissue 13 may require a relatively shallow cavity depth while ablation of the submucosal plexus may require an increased depth in order to capture a greater amount of tissue. In one embodiment, ablation probe 24F has a curved profile to better conform to a curvature of the exterior surface 13 of stomach 12.

When ablation probe 26F reaches one of ablation targets 14, 16, 18, and 19, the vacuum source activates to apply vacuum pressure to vacuum ports 54 to thereby draw the stomach tissue into cavity 51. The number and shape of vacuum ports 54, and the pressure applied by each vacuum port, may vary. While vacuum pressure is maintained, the surgeon extends conductive needle 56 into the captured stomach tissue. The depth of cavity 51 and the height of conductive needle 56 within the cavity influence the precise layer of tissue ablated.

In other embodiments the ablation energy may be laser, microwave, cryogenic, thermal, chemical, and the like to ablate cells within the captured tissue and the ablation probe may conform to the ablation energy source. In the embodiment shown in FIG. 7, the ablation energy is radio frequency electrical current applied to conductive needle 56. The electrical current may be selected to provide pulsed or sinusoidal waveforms, cutting waves, or blended waveforms. In addition, the electrical current may include ablation current followed by current sufficient to cauterize any blood vessels that may be compromised during the ablation process. Alternatively, in some embodiments, ablation probe 26F may take the form of a bipolar probe that carries two or more electrodes, in which case the current flows between the electrodes.

For ablation of various layers, the electrical current delivers power in the range of approximately 1 to 50 watts, and can be applied at a frequency of approximately 100 to 500 kHz, producing a temperature of approximately 50 to 100 degrees centigrade. To limit ablation of tissue to the target site, the ablation probe may include multiple temperature sensors for use in closed loop control of the ablation energy so that surrounding tissue can be maintained below 50 degrees centigrade.

The size of and volume of the ablated tissue can be controlled by selection of an appropriate level of electrical current, and may be further controlled by delivery of fluids to form a virtual electrode that extends into interstitial areas and creates a greater overall electrode surface for conduction of ablation energy.

Figure 8:
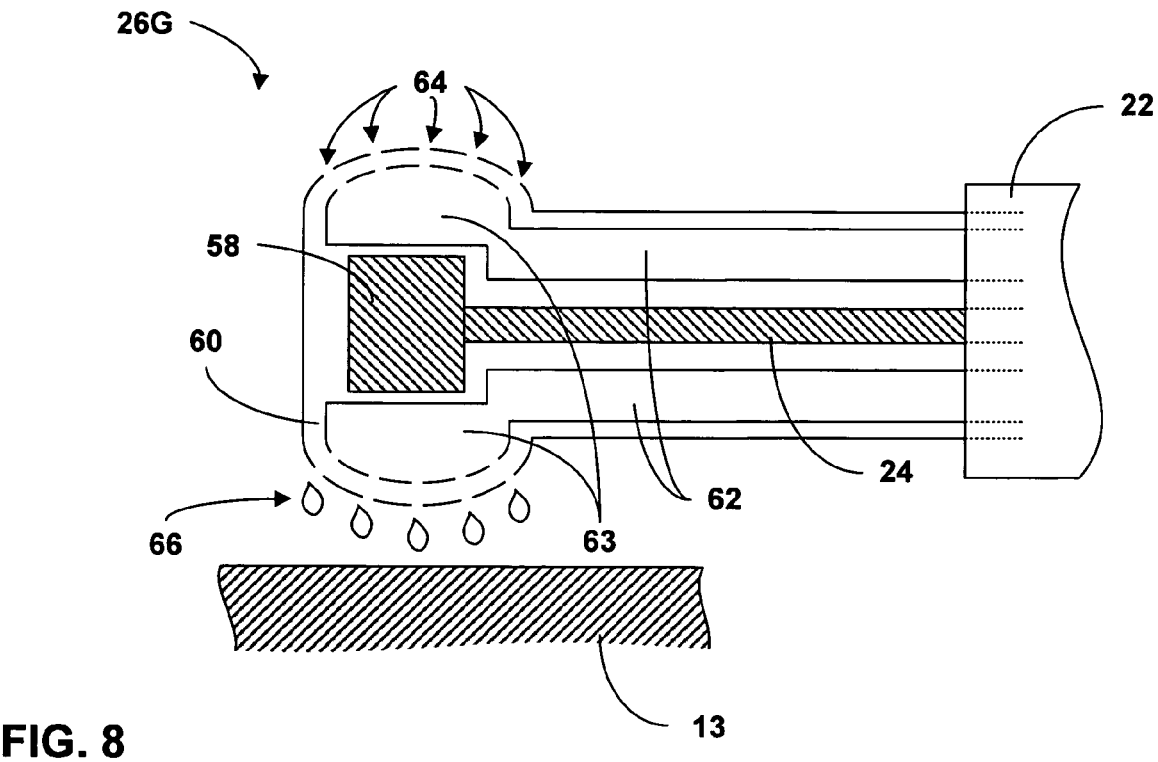
FIG. 8 is a side view illustrating an ablation probe comprising a porous balloon.

FIG. 8 is a side view illustrating an ablation probe 26G comprising a porous balloon 60. Ablation probe 26G includes an electrode 58, porous balloon 60, fluid channels 62, fluid chambers 63, and pores 64. Electrode 58 is coupled to ablation source 20, from FIG. 1, via electrical conductor 24. Porous balloon 60 is mounted about electrode 58. Balloon 60 defines pores 64 sized to permit a fluid 66 to leak at a relatively low flow rate from chambers 63. Fluid channels 62 deliver fluid to chambers 63 of balloon 60 to inflate the balloon. Balloon 60 may also have a temperature probe (not shown) located on an inside of the balloon so the fluid temperature can, if necessary, be precisely controlled.

Upon inflation of balloon 60, fluid 66 emits from pores 64, creating a collection of fluid 66 adjacent a tissue site of exterior surface 13. In other words, balloon 60 is inflated with conductive fluid 66, which is allowed to weep out of pores 64, effectively increasing the surface area of electrode 58. Additionally, the fluid that weeps through balloon 60 serves to distribute heat generated by electrode 58 more evenly across the target tissue. Pores 64 are significantly enlarged in FIG. 8 for purposes of illustration.

Figure 9:
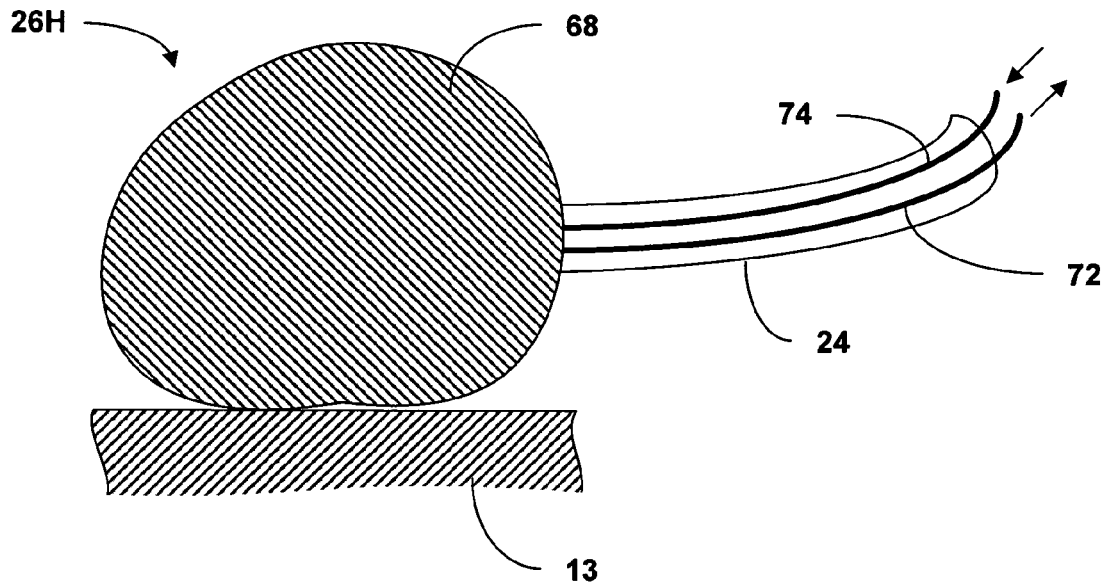
FIG. 9 is a diagram illustrating an ablation probe comprising a thermal balloon.

FIG. 9 is a diagram illustrating an ablation probe 26H comprising a thermal balloon 68. Ablation probe 26H includes thermal balloon 68, a fluid return 72, and a fluid supply 74. In the example shown in FIG. 9, conductor 24 conducts energy in the form of a thermal fluid received from ablation source 20, from FIG. 1. Fluid return and supply 72, 74 are coupled to ablation source 20. Thus, balloon 68 has an inlet and an outlet so fluid can be circulated from the external fluid source. The fluid source may provide either a hot fluid or a cryogenic fluid to ablation probe 26H. Conductor 24 may be thermally insulated to protect cannula 22 and prevent trauma to the abdominal cavity 10 of the patient.

When ablation probe 26H is placed proximate one of target regions 14, 16, 18, and 19, fluid, such as water heated to approximately 50 to 60 degrees centigrade or liquid nitrogen, is then circulated within balloon 68 for a period of time. The time period ranges from approximately 10 seconds to 10 minutes, depending on the temperature of the fluid, and the depth of ablation desired. The flexible balloon 68 conforms to the shape of the target region and thermal energy from the fluid is transmitted to exterior lining 13 of stomach 12 through the wall of balloon 68 to ablate the stomach tissue in the target region.

Figure 10:
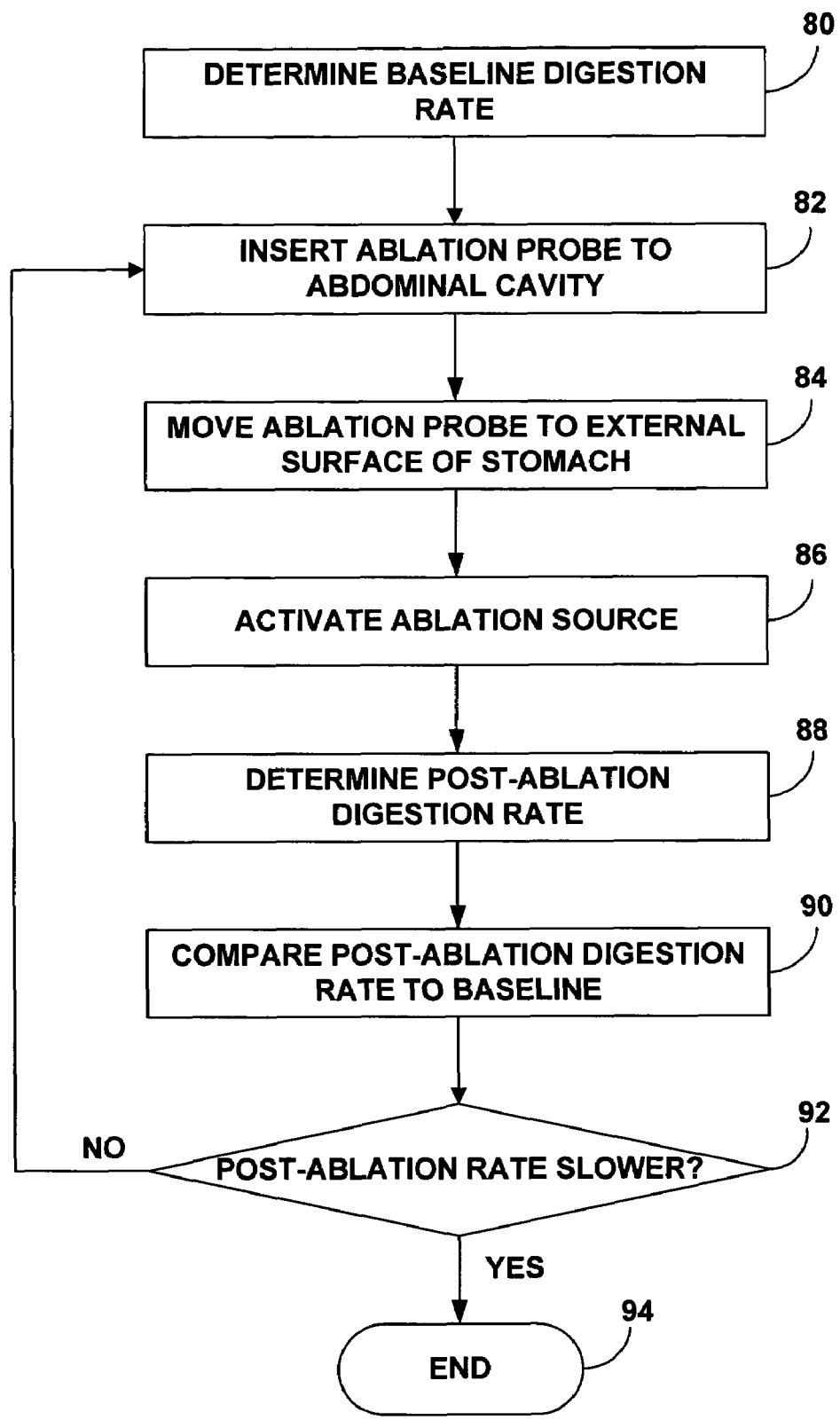
FIG. 10 is a flow diagram illustrating a method for ablation of exterior stomach lining to treat obesity.

FIG. 10 is a flow diagram illustrating a method for ablation of exterior stomach lining 13 to treat obesity. The method of FIG. 10 may make use of any of the ablation probes 26A-26H described herein. A baseline digestion rate of stomach 12 is determined (80) based on recordings from EGG monitor 28. Laparoscopic surgery is required to reach the exterior surface 13 of stomach 12. In laparoscopic surgery, the patient receives general anesthesia and one or more small incisions are made in an abdomen 10 of the patient. The abdominal cavity is inflated with carbon dioxide so a surgeon can see the abdominal organs. Ablation probe 26 is inserted into the abdominal cavity (82) of the patient through cannula 22 used in laparoscopic surgery. The ablation probe is moved proximate exterior surface 13 of stomach 12 (84). Ablation source 20 is activated (86) to deliver ablation energy to ablation probe 26 and exterior surface 13 to ablate stomach tissue that controls myoelectric activity.

A period of time after the ablation procedure, the anesthetic will wear off and the GI tract of the patient will regain full functionality. The post-ablation myoelectric activity in stomach 12 may then be recorded by EGG monitor 28 to determine a post-ablation digestion rate (88). The post-ablation digestion rate is compared to the baseline digestion rate (90). If the post-ablation digestion rate is slower than the baseline (92), the ablation procedure was effective and the obesity treatment may end (94). If the post-ablation digestion rate is not substantially slower than the baseline, the ablation procedure may be repeated. In that case, another laparoscopic surgery may be performed to ablate additional tissue and further alter myoelectric activity.

In other embodiments, steps may be added to the method shown in FIG. 10, including activating a vacuum source to immobilize a portion of exterior stomach lining 13 for ablation probe 26F. Additional examples include filling a balloon with fluid to either leak onto the stomach tissue prior to ablation as in ablation probe 26G, or to conduct thermal energy as in ablation probe 26H.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems for ablation, as described herein.

Furthermore, the invention may result in advantages other than or in addition to reduction of obesity. Ablating tissue on an exterior surface of a stomach of a patient in some patients can address disorders such as gastroparesis, nausea, or gastroesophageal reflux disease. After ablation, the impact of ablation upon these disorders can be assessed by monitoring gastric activity.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A method for treating obesity comprising ablating tissue on an exterior surface of a stomach of a patient with an ablation probe sized to fit the stomach and further comprising:
   monitoring gastric myoelectric activity of the stomach prior to the ablation to determine a baseline digestion rate;
   monitoring the gastric myoelectric activity of the stomach after the ablation to determine a post-ablation digestion rate; and
   ablating additional stomach tissue based on a comparison of the post-ablation digestion rate to the baseline digestion rate.

2. The method for treating obesity of claim 1, wherein monitoring gastric myoelectric activity comprises recording an electrogastrogram (EGG) of the patient.

3. The method for treating obesity of claim 1, wherein monitoring the gastric myoelectric activity of the stomach after the ablation comprises monitoring the gastric myoelectric activity of the stomach one week after the ablation.

4. The method for treating obesity of claim 1, wherein the baseline digestion rate comprises a baseline rate of gastric emptying and the post-ablation digestion rate comprises a post-ablation rate of gastric emptying.

5. The method for treating obesity of claim 1, wherein the comparison determines whether the ablation has slowed a peristaltic wave.

6. The method for treating obesity of claim 1, wherein ablating tissue comprises ablating at least a portion of at least one of a pacemaker region, interstitial cells of Cajal, smooth muscle cells, a splanchnic nerve, and a vagus nerve.

7. A method comprising:
  ablating tissue on an exterior surface of a stomach of a patient with an ablation probe sized to fit the stomach; and
  monitoring gastric activity of the stomach after the ablation, wherein monitoring gastric activity comprises assessing the impact of the ablation upon one of gastroparesis, nausea, and gastroesophageal reflax disease.

\* \* \* \* \*